(12) United States Patent
Minamoto et al.

(10) Patent No.: US 7,241,306 B2
(45) Date of Patent: Jul. 10, 2007

(54) NARROW-BAND UV-B PHOTOTHERAPEUTIC DEVICE

(75) Inventors: Maki Minamoto, Shinagawa-ku (JP); Yosuke Nishikage, Shinagawa-ku (JP); Akimichi Morita, Mizuho-ku (JP); Hisashi Yoshida, Shinagawa-ku (JP)

(73) Assignee: NEC Corporation, Tokyo (JP)

( * ) Notice: Subject to any disclaimer, the term of this patent is extended or adjusted under 35 U.S.C. 154(b) by 425 days.

(21) Appl. No.: 10/855,841

(22) Filed: May 28, 2004

(65) Prior Publication Data
US 2005/0010249 A1    Jan. 13, 2005

(30) Foreign Application Priority Data
May 29, 2003    (JP)    ............... 2003-152742

(51) Int. Cl.
*H01J 17/16*    (2006.01)
*H01J 1/62*    (2006.01)
(52) U.S. Cl. ............... 607/94; 313/486; 607/88
(58) Field of Classification Search ........ 313/484–486; 607/94
See application file for complete search history.

(56) References Cited

U.S. PATENT DOCUMENTS

| | | | |
|---|---|---|---|
| 4,370,595 A | | 1/1983 | Willemsen |
| 5,233,262 A | * | 8/1993 | Lynn et al. .............. 313/113 |
| 5,300,097 A | * | 4/1994 | Lerner et al. ............ 607/93 |
| 5,479,069 A | | 12/1995 | Winsor |
| 5,495,143 A | * | 2/1996 | Lengyel et al. ........... 313/574 |
| 5,686,789 A | * | 11/1997 | Schoenbach et al. ....... 313/491 |
| 6,294,867 B1 | * | 9/2001 | Lynn ..................... 313/422 |
| 6,590,319 B2 | * | 7/2003 | Moon .................... 313/292 |
| 6,731,058 B1 | * | 5/2004 | Kincade .................. 313/493 |
| 7,078,857 B2 | * | 7/2006 | Park ...................... 313/581 |
| 2002/0050780 A1 | | 5/2002 | Juestel et al. |
| 2002/0079827 A1 | * | 6/2002 | Park ...................... 313/485 |
| 2002/0161418 A1 | | 10/2002 | Wilkens et al. |

FOREIGN PATENT DOCUMENTS

| | | |
|---|---|---|
| EP | 1 067 166 A2 | 1/2001 |
| JP | 2001-299939 A | 10/2001 |
| WO | WO 98/51235 A1 | 11/1998 |

OTHER PUBLICATIONS

Morita, Akimichi, "Clinical Dermatology". vol. 56, No. 5 (2002 Supplement) pp. 106-111, Apr. 10, 2002, Igaku Shoin.
"Catalog of Narrow band UV-B Phototherapeutic Devices", May 2002, Clinical Supply KK.
Green C et al: "311 NM UVB Phototherapy an Effective Treatment for Psoriasis" British Journal of Dermatology, XX,XX, vol. 119, No. 6, Dec. 1988, pp. 691-696, XP009056323 ISSN: 0007-0963 *p. 692, lines 6-8; figure 1 *abstract.
Karvonen J et al: "311 NM UVB Lamps in the Treatment of Psoriasis With the Ingram Regimen" Acta Dermato-Venereologica, XX, XX, vol. 69, No. 1, 1989, pp. 82-85, XP009056322 ISSN: 0001-5555 *p. 82, last paragraph *p. 83; figure 2.

* cited by examiner

*Primary Examiner*—Henry M Johnson, III
(74) *Attorney, Agent, or Firm*—Sughrue Mion, PLLC

(57) ABSTRACT

A narrow-band UV-B phototherapeutic device includes: a light source unit that includes a fluorescent lamp of planar structure that is the ultraviolet light source for emitting narrow-band UV-B; a power supply for causing the fluorescent lamp to emit light; and a control unit for controlling the light emission of the fluorescent lamp.

12 Claims, 3 Drawing Sheets

NARROW-BAND UV-B PHOTOTHERAPEUTIC DEVICE

BACKGROUND OF THE INVENTION

1. Field of the Invention:

The present invention relates to a narrow-band UV-B phototherapeutic device that is effective in the treatment of such conditions as psoriasis, atopic dermatitis, and leukoderma, and more particularly to the configuration of a light source that includes a fluorescent lamp, i.e., the ultraviolet light source for emitting narrow-band UV-B.

2. Description of the Related Art:

Ultraviolet light can be defined as electromagnetic waves within the range of wavelengths that includes as its upper limit wavelengths of 360–400 nm, which is shortest wavelengths of visible light and as its lower limit wavelengths of 1 nm. Ultraviolet light can be divided according to wavelength into a long wavelength band UV-A, a middle-wavelength band UV-B, and a short wavelength band UV-C. Ultraviolet light has a sterilizing effect and is known for its use in the treatment of skin disorders. In particular, ultraviolet light having an extremely narrow wavelength of 311±2 nm in the middle-wavelength band is referred to as narrow-band UV-B. This narrow-band UV-B has a therapeutic effect against psoriasis that surpasses that of UV-B (broadband UV-B) that includes other wavelengths and can achieve a therapeutic effect of the same level as UV-A. In addition, narrow-band UV-B has a lower carcinogenic effect than broadband UV-B or UV-A, and in contrast with treatment that employs UV-A, causes no constitutional symptom side effects such as nausea or disorders of the liver and gastrointestinal tract. The results of research to date have clearly shown that narrow-band UV-B has these excellent properties, and in recent years, treatments of skin disorders that use narrow-band UV-B have become common in many countries including the United States. Greater detail is provided in a paper by Akimichi Morita in "Clinical Dermatology," Vol. 56, No. 5 (2002 Supplement) pages 106–111 (Apr. 10, 2002) published by Igaku Shoin.

Narrow-band UV-B phototherapeutic devices require an ultraviolet light source that emits ultraviolet light having a wavelength of 311±2 nm. As described in the above-described document, a fluorescent lamp (TL01) has been developed by Philips Holland as such an ultraviolet light source. This lamp is a straight-tube mercury-excited fluorescent ultraviolet lamp, and when used as the ultraviolet light source of a narrow-band UV-B phototherapeutic device, a plurality (10 in the example described in the above-referenced document) of lamps is arranged in parallel as the light source.

Typically, a phototherapeutic device requires that the intensity of the therapeutic light irradiated upon an affected area be uniform. This requirement arises due to the importance of avoiding a situation in which a particular area of affected areas that are simultaneously irradiated by light fails to receive the therapeutic effect due to insufficient irradiation, while other areas are subject to side effects due to excessive irradiation. This requirement is particularly important in a therapeutic device that uses light rays such as ultraviolet light having high energy.

Thus, in a narrow-band UV-B phototherapeutic device of the prior art that employs straight-tube ultraviolet fluorescent lamps, a plurality of fluorescent lamps are arranged in parallel within a plane to produce a planar light source in which the intensity of irradiated light is uniform. However, when the light source and treated area are close, it was impossible to avoid a situation in which the intensity of irradiation alternates regularly between strong and weak on the irradiated surface.

Distancing the light source from the treated area is a simple and effective method of dealing with this problem, and phototherapeutic devices of the prior art therefore normally irradiate the treated area from a distance. However, distancing the light source from the treated area also decreases the intensity of irradiation on the treated area. In particular, the UV-B ultraviolet light that is effective in the treatment of atopic dermatitis, psoriasis, and leukoderma is greatly attenuated in the air, and this attenuation drastically reduces the therapeutic effect and greatly extends the treatment time. Thus, the arrangement of a plurality of straight-tube fluorescent lamps was necessary to compensate for the reduction in the intensity of irradiation of the treated area in narrow-band UV-B phototherapeutic devices of the prior art. The intensity of emission of the light source was raised by using a plurality of fluorescent lamps.

For these reasons, a narrow-band UV-B phototherapeutic device of the prior art employing straight-tube fluorescent lamps could not avoid the necessity for a large light source and a lowered intensity of irradiation in the treated area. In addition, extra procedures such as masking areas other than the treated area were required to avoid the unnecessary exposure of healthy skin and the attendant serious, cancer-producing side effects. As a result, narrow-band UV-B phototherapeutic devices of the prior art have come to be mainly used in treatments that permit the extended treatment time that is necessary to compensate for the reduced intensity of irradiation of ultraviolet light and that also involve irradiation of ultraviolet light over a wide range, such as in the treatment of the entire body, the feet, the hands and the head. Even in such cases, however, patients must endure extended treatment time, the discomfort of remaining in the same position for an extended period of time during treatment, the inability to do anything else during treatment, and the great restrictions on daily routine.

SUMMARY OF THE INVENTION

It is an object of the present invention to provide a narrow-band UV-B phototherapeutic device that delivers narrow-band UV-B irradiation of higher intensity and thus allows a shorter treatment time, and that can therefore reduce the burden imposed on patients.

It is another object of the present invention to provide a narrow-band UV-B phototherapeutic device that, when used directly, can prevent unnecessary ultraviolet exposure of healthy skin without necessitating such procedures as masking areas other than the treatment area, that causes fewer side effects, and that is compact and safe.

The narrow-band UV-B phototherapeutic device of the present invention is a narrow-band UV-B phototherapeutic device for treating an affected area by irradiating narrow-band UV-B. The narrow-band UV-B phototherapeutic device of the present invention includes: a light source unit that includes a fluorescent lamp, this being the ultraviolet light source for emitting narrow-band UV-B; a power supply for causing the fluorescent lamp to emit light; and a control unit for controlling the light emission of the fluorescent lamp. The fluorescent lamp that emits narrow-band UV-B is a lamp of planar structure.

The above and other objects, features, and advantages of the present invention will become apparent from the following description with reference to the accompanying drawings, which illustrate examples of the present invention.

DETAILED DESCRIPTION OF THE PREFERRED EMBODIMENTS

Figure 1:
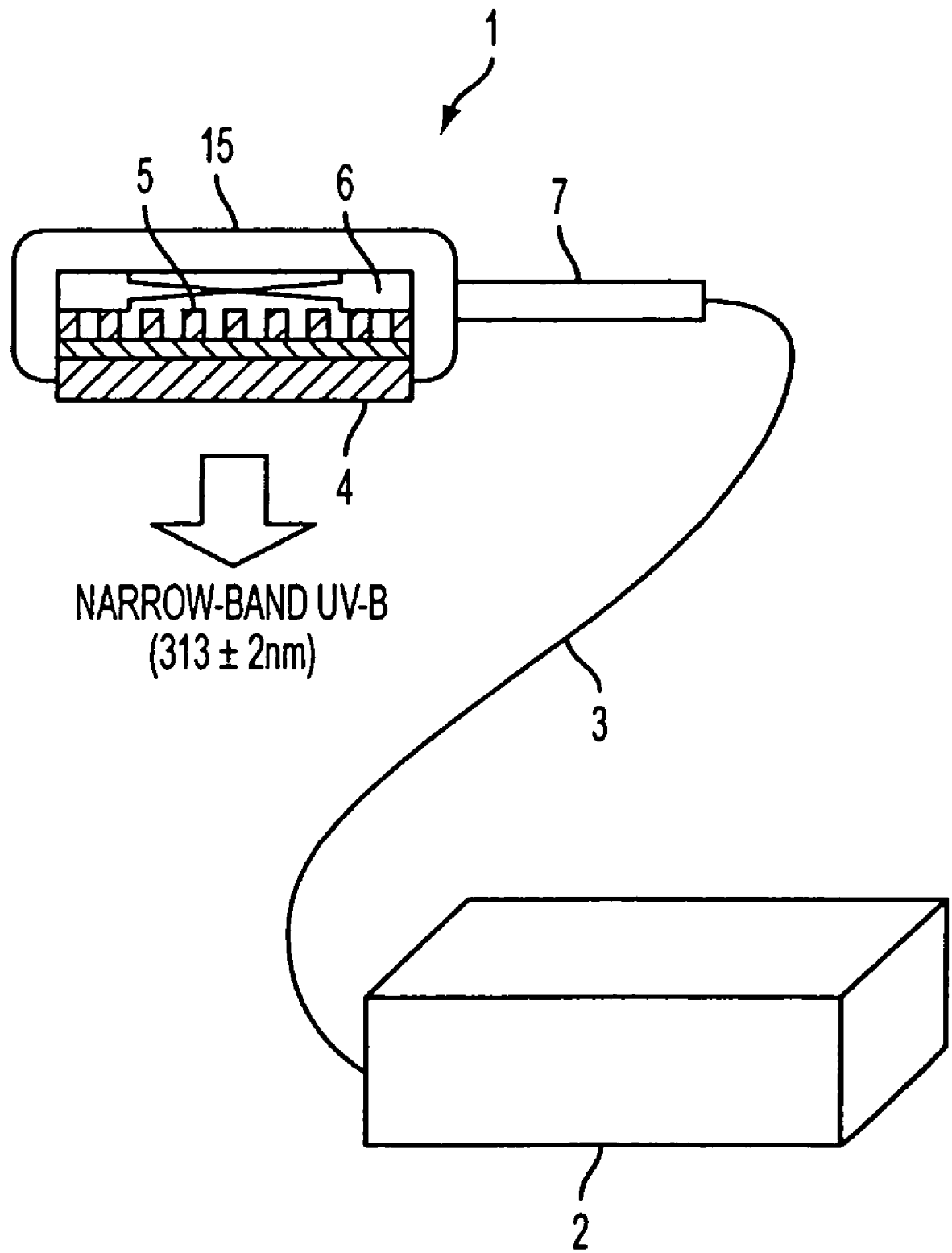
FIG. 1 is a view of the configuration of the narrow-band UV-B phototherapeutic device according to an embodiment of the present invention.

FIG. 1 shows the configuration of a narrow-band UV-B phototherapeutic device according to an embodiment of the present invention. The ultraviolet phototherapeutic device is composed of light source unit 1 and control/power supply unit 2; light source unit 1 and control/power supply unit 2 being connected by cord 3.

Light source unit 1 is a structure in which ultraviolet fluorescent lamp 4 and a forced-air cooling device are incorporated in case 15. As will be explained hereinbelow, ultraviolet fluorescent lamp 4 is a discharge lamp of planar structure, is supplied with high-frequency ac power from control/power supply unit 2 by way of cord 3, and discharges narrow-band UV-B having a sharp peak at a wavelength 313 nm in the downward direction of the figure. A forced-air cooling device is provided on the back surface (the surface opposite the side from which UV-B is released) of ultraviolet fluorescent lamp 4. This forced-air cooling device is composed of cooling fins 5 and supply fan 6. Handle 7 is provided on case 15 for holding and moving light source unit 1 by hand or for securing the device in a support. Handle 7 also receives cord 3 from control/power supply unit 2.

Control/power supply unit 2 is constructed to accommodate the control unit for controlling the operation of ultraviolet fluorescent lamp 4 and the power supply unit for supplying the power necessary for lighting ultraviolet fluorescent lamp 4. Although a detailed explanation of the control unit and power supply unit is omitted, the control unit is equipped with at least a circuit such as an inverter for generating a high-frequency ac voltage for lighting ultraviolet fluorescent lamp 4. If necessary, the control unit is also equipped with, for example, a timer function for determining the duration of irradiation. The power supply unit supplies power to the above-described control unit, and if ultraviolet fluorescent lamp 4 is lighted by an inverter, is equipped with at least a circuit for generating a dc voltage of, for example, about 5 V that is necessary for the operation of the inverter from a 100-V ac commercial power supply.

Figure 2A:
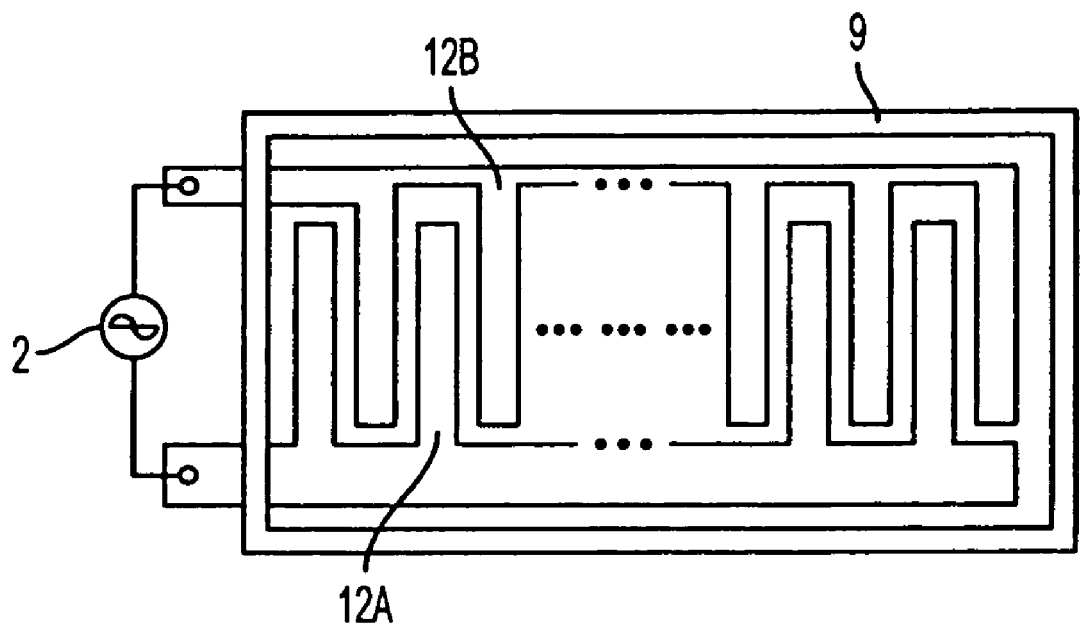
FIG. 2A shows a plan view of the ultraviolet fluorescent lamp of planar structure according to an embodiment of the present invention.
Figure 2B:
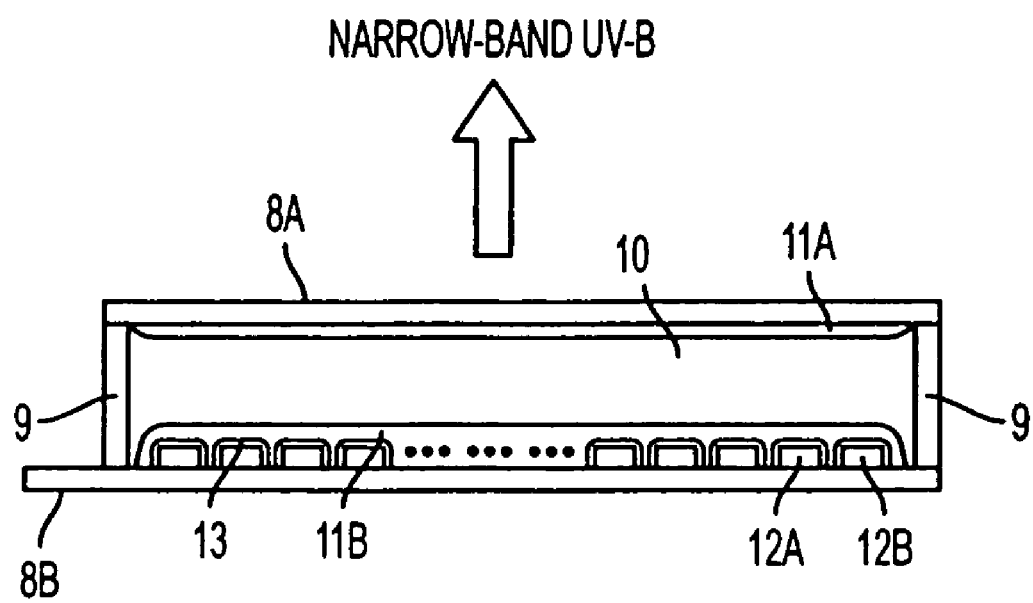
FIG. 2B shows a sectional view of the ultraviolet fluorescent lamp of planar structure according to an embodiment of the present invention.

FIGS. 2A and 2B show a plan view and a sectional view of an ultraviolet fluorescent lamp of planar structure according to the present embodiment respectively. Ultraviolet fluorescent lamp 4, which is the narrow-band UV-B light source, is equipped with two confronting planes (ultraviolet light-emitting side substrate 8A and rear substrate 8B), and frame-shaped sealing glass 9 is interposed between these two substrates along the edges of the two substrates.

Each of the two substrates 8A and 8B and sealing glass 9 is hermetically sealed, the two substrates and sealing glass 9 thus forming airtight discharge chamber 10. Discharge chamber 10 is charged with a discharge medium gas at a total pressure of, for example, 10–300 Torr. The discharge medium gas is 100% rare gas such as xenon or a gas mixture of xenon and another rare gas such as neon or argon; and in contrast with the mercury-excited ultraviolet fluorescent lamp that is employed in narrow-band UV-B phototherapeutic devices of the prior art, does not include mercury vapor.

Ultraviolet light-emitting side substrate 8A is composed of ultraviolet-permeable glass that transmits light having a wavelength of 300 nm or more, and ultraviolet luminescent phosphor layer 11A is formed on the surface that is directed toward discharge chamber 10. Ultraviolet luminescent phosphor layer 11A is a known gadolinium-activated phosphor, and may be an ultraviolet luminescent phosphor for vacuum ultraviolet excitation such as a $YF_3$: Gd and Pr phosphor, a $YBO_3$: Gd and Pr phosphor, a $YB_xO_y$: Gd and Pr phosphor (where x and y are any value), or a $(Y_{1-x}Gd_x)Al_3(BO_3)_4$ (where $0 < x \leq 1$) phosphor that are disclosed in, for example, Japanese Patent Laid-Open Publication No. 2001-081460, Japanese Patent Laid-Open Publication No. 2001-172624, and Japanese Patent Laid-Open Publication No. 2002-348571, or a mixture of these phosphors. The thickness of ultraviolet luminescent phosphor layer 11A is, for example, 20–50 μm. The praseodymium (Pr) content is not essential as long as the ultraviolet luminescent phosphor is a gadolinium-activated phosphor and strongly emits UV-B.

Rear substrate 8B is provided with a pair of electrodes 12A and 12B on the inner wall that is on the discharge chamber side. These two electrodes are both planar comb-shaped electrodes and are arranged with the tooth portions of the two electrodes mutually opposed and with the teeth of each electrode being inserted between the teeth of the other electrode. Dielectric layer 13 having silica as a chief component is formed on electrodes 12A and 12B. Ultraviolet luminescent phosphor layer 11B composed of the same material as the above-described ultraviolet luminescent Phosphor is further formed over dielectric layer 13.

When a sine-wave or rectangular-wave ac high-voltage having a frequency on the order of 10–100 kHz and a voltage on the order of several kV is applied across the two electrodes 12A and 12B from the inverter in control/power supply unit 2, a dielectric barrier discharge that takes silica layer 13 as a dielectric is generated in discharge chamber 10, whereupon the discharge medium, i.e., xenon, radiates ultraviolet light. The ultraviolet light having a principal wavelength of 147 nm that is radiated by xenon then excite Ultraviolet luminescent phosphor layer 11A and 11B, whereby narrow-band UV-B is emitted that has a sharp peak having a half-width of 5 nm or less at a wavelength 313 nm, such as is shown by the spectrum of emitted light in FIG. 3.

The narrow-band UV-B phototherapeutic device according to the present invention uses an ultraviolet fluorescent lamp of planar structure and having comb electrodes as the narrow-band UV-B light source. As will be explained hereinbelow, electrodes 12A and 12B are pattern-formed by screen printing a conductive paste having high conductivity such as silver or copper, and these electrodes are therefore amenable to micro-processing, and the width of the comb teeth portions of each electrode as well as the space between adjacent comb teeth can easily be made as small as several tens of μm. Still further, formation on the sub-micrometer order can be achieved through the use of, for example, a combination of a conductive film formation techniques using sputtering and photolithography. Accordingly, if the irradiation intensity is expressed by, for example, the spacing of rays of equal intensity, the present invention enables a dramatic improvement in the uniformity of the irradiation intensity immediately adjacent to the light source as compared to the narrow-band UV-B phototherapeutic device of the prior art that employed straight-tube fluorescent lamps as the light source and that, limited by the tube diameter of the lamp, could not surpass the order of several mm. Expressed in the strongest terms, the irradiation intensity is uniform to the extent that the light source lamp may be placed in direct contact with the treated area. The irradiation intensity with respect to the treated area is thus markedly improved. As an example, in the case of a narrow-band UV-B phototherapeutic device of the prior art in which ten straight-tube mercury-excited fluorescent ultraviolet lamps are aligned as the ultraviolet light source, the irradiation intensity of the narrow-band UV-B upon a treated area when the treated area is fixed at a position 25–50 cm away from the light source lamps was approximately 3–5 mW/cm$^2$. In contrast, in the case of a therapeutic device according to the present embodiment, a irradiation intensity of approximately 20 mW/cm$^2$ was obtained, and the duration of treatment for each point of the treated area was reduced to from one-quarter to one-fifth the time of the prior art.

The narrow-band UV-B phototherapeutic device according to the present embodiment allows irradiation in the immediate proximity of a treated area, and the size of the light source can therefore be made the same size as the area of the treated area, and the treated area can thus be subjected to spot irradiation. As a result, the unnecessary exposure of healthy skin can be avoided without resorting to special measures such as masking. The possibility of making light source unit 1 more compact, together with the configuration in which control/power supply unit 2 and light source unit 1 are connected by cord 3, have the merit of enabling treatment in small treatment rooms that until now could not accommodate the installation of phototherapeutic devices.

Figure 3:
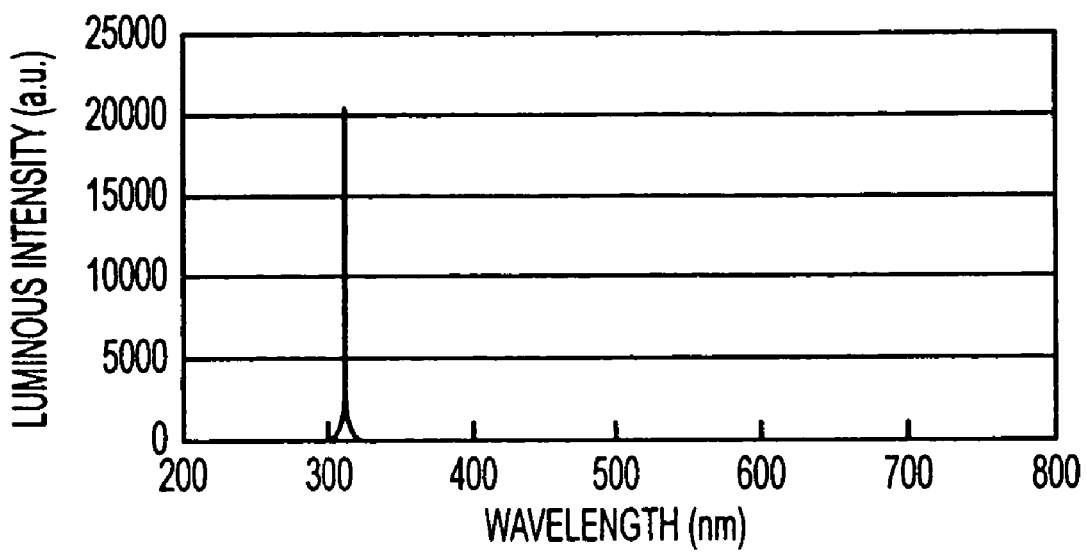
FIG. 3 shows the spectrum of emitted light of the gadolinium-activated ultraviolet phosphor that is used in the ultraviolet fluorescent lamp according to an embodiment of the present invention.

The light source lamp of the narrow-band UV-B phototherapeutic device according to the present embodiment does not include mercury vapor in the discharge medium gas, and further, the ultraviolet luminescent Phosphor emits only narrow-band UV-B having a sharp peak at a wavelength of 313 nm, such as is shown by the spectrum of emitted light in FIG. 3. There is consequently no need to block the 254 nm ultraviolet light generated from mercury that is not used in treatment and still harmful to the human body, and the need for costly filters for cutting harmful ultraviolet light is thus eliminated, enabling a corresponding reduction in costs.

Figure 4:
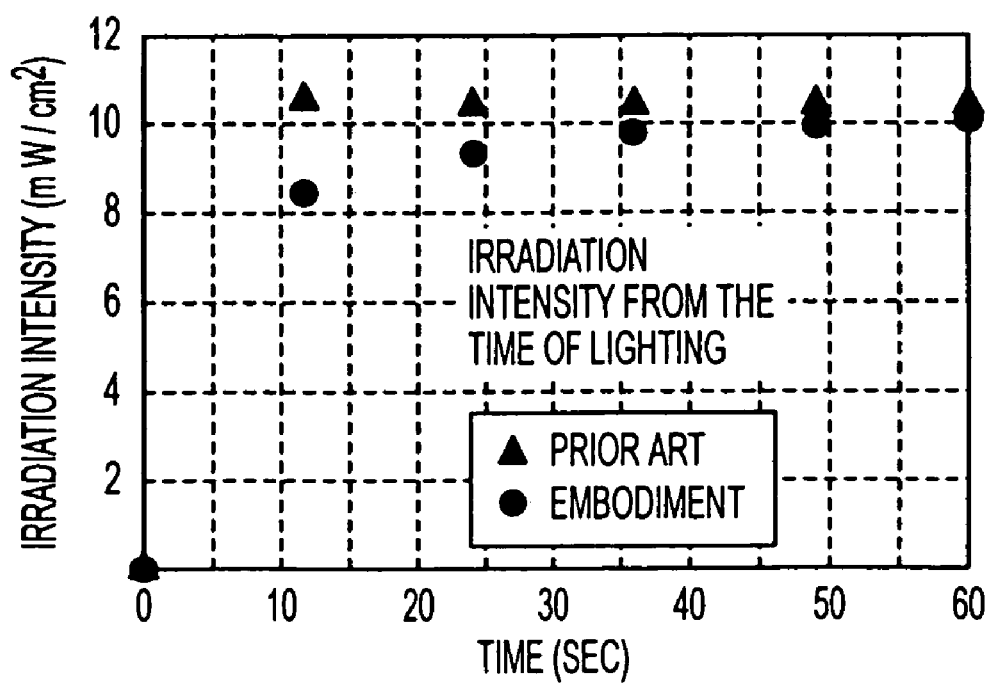
FIG. 4 shows a comparison of the irradiation intensity rise properties immediately following the initiation of discharge in a mercury-excited ultraviolet fluorescent lamp and the ultraviolet fluorescent lamp according to an embodiment of the present invention.

In mercury fluorescent lamps, moreover, the need for a certain amount of time for the mercury vapor.inside the tube to stabilize immediately after lighting and the slow rise of the irradiation intensity are well known. In contrast, the light source lamp of the phototherapeutic device according to the present embodiment does not contain mercury vapor and instead takes a rare gas such as xenon as the discharge medium, whereby instant lighting is possible and the rise to irradiation intensity immediately after lighting is therefore rapid. As an example, FIG. 4 shows a comparison of the luminous intensity rise characteristic immediately after lighting for a mercury fluorescent lamp (Philips TL01 mercury-excited fluorescent ultraviolet lamp) that is used in a narrow-band UV-B phototherapeutic device of the prior art and for the ultraviolet fluorescent lamp of planar structure according to the present embodiment. As can be seen from FIG. 4, the mercury fluorescent lamp of the prior art requires at least 50 seconds from the time of lighting until stabilization of the luminous intensity, whereas the planar ultraviolet fluorescent lamp according to the present embodiment reaches 100% luminous intensity in approximately 12 seconds. As a result, a phototherapeutic device that uses the mercury fluorescent lamp of the prior art necessitates the prior lighting of the lamp for treatment, and this need in turn results in significant increases in cost for operation and maintenance due to the large loss of power and the need for frequent replacement of fluorescent lamps. In contrast, the narrow-band UV-B phototherapeutic device according to the present embodiment can light instantly and therefore needs to be lighted only when in actual use, and thus provides a large cost-cutting effect.

The use of gas that does not contain mercury vapor in the ultraviolet fluorescent lamp that is used as the light source can also serve to prevent any harmful effects of mercury on the human body that might occur when a lamp breaks, and further, contributes to a reduction of harmful effects on the environment.

The use of a lamp of planar structure in the ultraviolet fluorescent lamp that is the light source in the narrow-band UV-B phototherapeutic device according to the present embodiment enables an increase in the irradiation intensity of the narrow-band UV-B on the treated area, and the installation of a forced cooling device on the rear surface of fluorescent lamp 4 improves the heat discharge of the lamp and enables an increase in the power that is supplied to the lamp. As a result, the radiation intensity of the light source itself can be further increased to enable a further increase in the irradiation intensity upon the treated area. As an example of the forced cooling device in the present embodiment, a forced-air cooling device is shown in which air is blown by supply fan 6 against cooling fins 5 as shown in FIG. 1, but a configuration may also be used in which supply fan 6 is replaced by an exhaust fan and heat is released from cooling fins 5. The fins and fan may of course each be used independently. Still further, a cooling element that employs the thermo-electric phenomenon such as a Peltier-effect element may also be used in place of the fan and fins.

The narrow-band UV-B phototherapeutic device according to the present embodiment may be constructed by known fluorescent lamp fabrication techniques. As an example, the inventors fabricated a narrow-band UV-B phototherapeutic device by the methods described hereinbelow.

A plate of soda glass that was to become rear substrate 8B was first prepared, and two electrodes 12A and 12B were formed on one surface of this glass plate. The patterns of the two electrodes 12A and 12B were first formed on the surface of the glass plate by means of screen-printing using, as the electrode material, a conductive paste that employs silver or copper as the electrical conducting material, and the patterns were then sintered. Instead of the screen-printing method, the electrodes can also be formed by forming a conductive film by sputtering and forming patterns by photolithography. An insulating paste having silica as its chief ingredient was next screen printed on the two electrodes 12A and 12B and then sintered to form dielectric layer 13. Ultraviolet luminescent phosphor layer 11B was further formed on dielectric layer 13 by the same screen-printing method to obtain rear substrate 8B. The previously described gadolinium (Gd)-activated phosphor was used for the ultraviolet luminescent phosphor.

In order to fabricate ultraviolet light-emitting side substrate 8A, an ultraviolet-permeable glass plate was next prepared and ultraviolet luminescent phosphor layer 11A formed on this glass plate to a thickness of 20–50 μm. An ultraviolet luminescent phosphor of the same gadolinium-activated phosphor as used on rear substrate 8B was applied to the glass plate by means of screen printing and then sintered.

In addition, sealing glass 9 was prepared in a frame shape made from low-melting-point glass.

Ultraviolet light-emitting side glass substrate 8A and rear glass substrate 8B were then arranged in confrontation with each other with the phosphor layer-covered surfaces directed inward and sealing glass 9 was interposed, following which sealing glass 9 was fused to ultraviolet light-emitting side substrate 8A and fused to rear substrate 8B respectively. The two glass substrates, i.e., the ultraviolet light-emitting side and the rear side, may also be directly fused together without the interposition of sealing glass 9.

The interior of discharge chamber 10 that is created by sealing glass 9 and the two glass substrates 8A and 8B was next evacuated and then charged with xenon gas to a pressure of 20 Torr.

Finally, cooling fins 5 were affixed to the outside surface of rear substrate 8B and supply fan 6 was additionally attached to complete light source unit 1; and light source unit 1 was then connected by cord 3 to control/power supply unit 2, which was prepared separately, to complete the narrow-band UV-B phototherapeutic device according to the present embodiment.

In the present embodiment, an example was described in which ultraviolet luminescent phosphor layer 11B was provided on dielectric layer 13 that covers electrodes 12A and 12B on rear substrate 8B, but the present invention is not limited to this embodiment. Ultraviolet luminescent phosphor layer 11B need not be provided on rear substrate 8B, and, for example, a field emission material (a material that emits electrons under the force of a field) such as a layer of magnesium oxide may be provided on dielectric layer 13 in place of ultraviolet luminescent phosphor layer 11B. Alternatively, a field emission layer and a phosphor layer may be stacked as a multilayer structure. Modifications are possible within the scope of a composition for causing discharge in discharge chamber 10 that includes a pair of electrodes 12A and 12B and dielectric layer 13 that covers these electrodes.

Further, as the planar ultraviolet fluorescent lamp that serves as the light source, an example was described for an internal-electrode lamp having a configuration in which electrodes 12A and 12B are provided on the inner surface (the surface that is directed toward discharge chamber 10) of rear substrate 8B. However, the same effect as the internal-electrode lamp is also be obtained in a lamp having an external-electrode configuration in which both electrodes are provided on the external surface (the surface on which cooling fins 5 and supply fan 6 are provided). In a fluorescent lamp of the external-electrode configuration, the glass plate that is the substrate of rear substrate 8B itself acts as the dielectric for causing dielectric barrier discharge inside the discharge chamber, and this configuration thus eliminates any particular need for dielectric layer 13 (see FIG. 2) that is provided in the internal-electrode configuration of fluorescent lamp. In the external-electrode form of the fluorescent lamp, the electrodes are formed on the outer surface of rear substrate 8B, and this configuration therefore requires reliable insulation to ensure safety when handling, but in contrast with a fluorescent lamp of the internal-electrode form, this configuration eliminates the consumption of electrodes due to sputter resulting from discharge and therefore features a longer lamp life, resulting in less frequent exchange and a reduction of maintenance costs.

Although a certain preferred embodiment of the present invention has been shown and described in detail, it should be understood that various changes and modifications may be made without departing from the spirit or scope of the appended claims.

What is claimed is:

1. A narrow-band UV-B phototherapeutic device for treating an area requiring treatment by irradiating narrow-band UV-B, comprising:
    a light source unit that includes a fluorescent lamp of planar structure, said fluorescent lamp being an ultraviolet ray source for emitting narrow-band UV-B;
    a power supply for causing said fluorescent lamp to emit light; and
    a control unit for controlling light emission of said fluorescent lamp;
    wherein said fluorescent lamp of planar structure comprises:
    a first substrate that is a flat plane in shape and that is permeable to ultraviolet rays;
    a second substrate that is a flat plane in shape and that confronts said first substrate across an interposed gap;
    a discharge chamber that is formed by hermetic sealing of perimeters of said first substrate and said second substrate;
    a discharge medium gas that is charged in said discharge chamber; and
    a pair of electrodes that are both provided on said second substrate for causing discharge inside said discharge chamber;
    wherein a cooling device for cooling said fluorescent lamp is provided on an external side of said second substrate.

2. A narrow-band UV-B phototherapeutic device according to claim 1, wherein each of said pair of electrodes has a planar toothed comb shape and is arranged such that toothed portions are mutually opposed and said teeth of each electrode are inserted between said teeth of other electrodes.

3. A narrow-band UV-B phototherapeutic device according to claim 2, wherein both of said pair of electrodes are provided on a surface of said second substrate that is directed toward said discharge chamber.

4. A narrow-band UV-B phototherapeutic device according to claim 2, wherein both of said pair of electrodes are provided on a surface of said second substrate that is opposite a side that is directed toward said discharge chamber.

5. A narrow-band UV-B phototherapeutic device according to claim 1, wherein said cooling device is an air-cooling device that includes at least either one of fins and a fan.

6. A narrow-band UV-B phototherapeutic device according to claim 1, wherein said cooling device includes a Peltier-effect element.

7. A narrow-band UV-B phototherapeutic device according to claim 1, wherein said light source unit is separated from said power supply and said control unit and is electrically connected to said power supply and said control unit by a cord.

8. A narrow-band UV-B phototherapeutic device according to claim 1, wherein a gas of said discharge medium is composed of only a rare gas.

9. A narrow-band UV-B phototherapeutic device according to claim 1, wherein said fluorescent lamp of planar structure has an emitted light spectrum having a peak with a half-width of 5 nm or less at a wavelength 313 nm.

10. A narrow-band UV-B phototherapeutic device according to claim 1, wherein said fluorescent lamp of planar structure includes a gadolinium-activated ultraviolet luminescent phosphor.

11. A narrow-band UV-B phototherapeutic device according to claim 10, wherein said ultraviolet luminescent phosphor is:

an ultraviolet luminescent phosphor having a compositional formula expressed by any one of:

$YE_3$: Gd;

$YBO_3$: Gd;

$YB_xO_y$: Gd (where x and y are any values); and $(Y_{1-x}Gd_x)Al_3(BO_3)_4$ (where $0<x\leq1$); or a phosphor mixture of at least two of the ultraviolet luminescent phosphors.

12. A narrow-band UV-B phototherapeutic device according to claim 11, wherein said ultraviolet luminescent phosphor that is expressed by said compositional formulas contains praseodymium.

* * * * *